United States Patent [19]
Fairleigh

[11] Patent Number: 5,997,176
[45] Date of Patent: Dec. 7, 1999

[54] X-RAY METHOD AND APPARATUS

[76] Inventor: James F. Fairleigh, 603 Richmond La., Friendswood, Tex. 77546

[21] Appl. No.: 09/189,665

[22] Filed: Nov. 11, 1998

[51] Int. Cl.[6] ........................................................ H05G 1/02
[52] U.S. Cl. .............................. 378/196; 378/38; 378/195
[58] Field of Search .................................. 378/38, 39, 40, 378/193, 195, 196, 197, 198, 208, 209

[56] References Cited

U.S. PATENT DOCUMENTS

| | | | |
|---|---|---|---|
| 3,281,598 | 10/1966 | Hollstein | 378/196 |
| 4,503,552 | 3/1985 | Miyahara et al. | 378/196 |
| 4,566,444 | 1/1986 | Spolyar | 128/303 B |
| 4,573,917 | 3/1986 | Erickson | 433/75 |
| 4,579,117 | 4/1986 | Spolyar | 128/303 B |
| 4,616,998 | 10/1986 | Wong | 433/73 |
| 4,641,336 | 2/1987 | Gastrin | 378/156 |
| 4,683,582 | 7/1987 | Spolyar | 378/174 |
| 4,759,361 | 7/1988 | Gallop et al. | 128/303 B |
| 4,760,591 | 7/1988 | Gallop et al. | 378/170 |
| 4,783,793 | 11/1988 | Virta et al. | 378/39 |
| 4,831,645 | 5/1989 | Guenther et al. | 378/205 |
| 5,148,454 | 9/1992 | Coffman | 378/40 |
| 5,263,494 | 11/1993 | Margelos et al. | 128/845 |
| 5,281,135 | 1/1994 | Schwestka-Polly | 433/56 |
| 5,408,521 | 4/1995 | Grady | 378/96 |
| 5,454,023 | 9/1995 | Asikainen | 378/156 |

OTHER PUBLICATIONS

Pelton & Crane, A Siemens Company, Dental Products Division, "Orthophos® Plus," pp. 1–4, Charlotte, North Carolina, Oct. 1992.

Pelton & Crane, A Siemens Company, Dental Products Division, "The New Epoch. Heliodent DS," pp. 1–11, Charlotte, North Carolina, Aug. 1996.

Pelton & Crane, A Siemens Company, Dental Products Division, "Orthophos® 3 Diagnostic Imaging System," Charlotte, North Carolina, Jun. 1994.

Planmeca Company, "Prosytle Intraoral X–ray," pp. 1–2, Wood Dale, Illinois, Feb. 14, 1997.

Planmeca Company, "Prostyle Intra–Technical Specifications," pp. 1–2, Wood Dale, Illinois, Mar. 14, 1997.

Planmeca Company, "PM 2002 EC Proline," pp. 1–8, Helsinki, Finland, 1997.

*Primary Examiner*—Daivd P. Porta
*Attorney, Agent, or Firm*—Akin, Gump, Strauss, Hauer & Feld

[57] ABSTRACT

A method and an x-ray apparatus produces a standard set of x-rays of a person's head while he or she is in a prone position. A movable frame is rigidly connected to a table, such as an operating table, and an extendible arm having a receiver for an x-ray source at a distal end provides for placement of the x-ray source in various, fixed positions. Right and left lateral cephalograms, an anterior-to-posterior cephalogram, and right and left transcranial views of the temporomandibular joint are provided by the fixed-position x-ray source. A panorama x-ray machine is also movably engaged with the frame for taking panographic images. A first set of cephalograms can be taken of a patient on an operating table, and the portable x-ray apparatus can be moved away from the operating table. A surgical treatment objective can be overlaid on the first set of cephalograms. Oral or orthognathic surgery or repair can be performed, and the portable x-ray apparatus can be subsequently reconnected to the operating table for taking a second set of cephalograms that precisely overlay the first set. A surgical team can thus compare actual operative results with the surgical treatment objective, and if necessary, make changes while the patient is still on the operating table.

44 Claims, 8 Drawing Sheets

X-RAY METHOD AND APPARATUS

BACKGROUND OF THE INVENTION

1. Field of the Invention

This invention pertains to a method and an apparatus for taking x-rays and more particularly to a method and an apparatus for providing a reproducible set of x-rays of a patient in a prone position.

2. Description of the Related Art

A set of x-rays is taken before orthognathic surgery, which is surgery to reposition the bones of the face and jaw. A surgical treatment objective is developed and traced onto x-ray films to provide a plan for movement of hard tissues in and around a person's jaw. A second set of x-rays is taken after the surgery, but typically a couple of days after the surgery, when the patient is able to stand or sit for orthodontic x-rays. The post-surgery x-rays are compared to the surgical treatment objective to determine whether the desired results were achieved. If the desired results were not achieved, then the patient must be operated on a second time, leading to the additional risk, discomfort and expense of a second surgical procedure. Even a very small deviation between a desired result and an actual result can be unacceptable because misalignment of a person's jawbone can result in poor cosmetic and functional result and temporomandibular joint pain.

The need for orthognathic surgery typically arises as a procedure for correcting an improper location of jawbones or teeth. Victims of trauma to the face, such as victims of car accidents and gun shot wounds, also have a need for pre-surgery and post-surgery x-rays of the jawbones and teeth. Trauma victims and other persons, such as invalids, are frequently unable to stand or sit while a set of orthodontic x-rays are taken. It is thus necessary to take the x-ray while the person is in a prone position, such as on an operating table. However, x-rays currently taken of a patient in a prone position differ in magnification and orientation from one set of images to a second set of images taken subsequent in time.

In U.S. Pat. Nos. 4,566,444; 4,579,117; and 4,683,582, issued to Spolyar, a portable cephalostat is disclosed as having a frame-like base sub-assembly that provides an area upon which a patient's head can rest. The base sub-assembly provides a support for supporting locating arms that serve to locate the patient's head in a selected position. An x-ray film is secured to the base sub-assembly in various positions, one below the patient's head and others on each side of the head generally parallel to a mid-sagittal plane of the patient's head. Spolyar provides a telescoping rod, resembling an antennae, as an indicator of a desired location for an anode of an x-ray machine. Spolyar also discloses calculations for determining a degree of magnification on an x-ray film, which is related to distances between the film and the patient and the patient and the anode of the x-ray machine. There is no rigid capture of the patient's head relative to an x-ray source. X-ray films taken subsequent in time are not sufficiently identical to x-rays taken earlier in time. The level of precision is inadequate.

U.S. Pat. No. 5,148,454, issued to Coffman, discloses an apparatus for conducting cranial x-ray tomography and radiography. An apparatus is disclosed having a horizontally oriented, motor driven rotatable shaft for imparting controlled rotation to an elongate support member having an x-ray source and a film holder provided at an opposite end. The apparatus includes a cephalometer that supports a patient's head at a fixed position during x-ray tomography and radiography procedures. However, the apparatus is not portable and is not suitable for taking x-rays of a patient in a prone position.

U.S. Pat. No. 4,831,645, issued to Guenther et al., discloses an apparatus for positioning the head of a patient for producing dental panorama tomograms. The apparatus has an arrangement for positioning the head in a desired position relative to a fixed point with respect to at least one projection plane. This point in turn assumes a definite position relative to a central ray extending from an x-ray tube towards an x-ray picture. A silhouette of the head is produced and projected, and an actual position is compared to a desired position. The head is moved until the silhouette of the actual position is congruent with the silhouette of the desired position, which brings the head into the desired position for x-ray exposure.

U.S. Pat. No. 4,759,361, issued to Gallop et al., discloses a telescoping adjustment assembly for a head positioner used in a cephalostat. A cephalostat housing has a pair of ear posts carried outwardly of the cephalostat housing and moveable toward the cephalostat housing so that the mid-sagittal of the head may be repetitively positioned in a same alignment to obtain a consistent series of radiographs over time. A patient's dentition and temporomandibular joint can be located in virtually the same arrangement relative to the film for x-rays taken at different times, such as for determining a patient's progress during orthodontia. However, the apparatus has a wall plate support for attachment to a wall and is thus not portable or suitable for use in an operating room.

U.S. Pat. No. 4,783,793, issued to Virtia et al., discloses a panoramic tomography x-ray apparatus such as for obtaining images of dental systems. An x-ray tube of an x-ray generator and an x-ray film cartridge are mounted to an arm that is rotatable. A control system for controlling the functioning of the equipment and apparatus on the basis of control data and a pre-stored program are disclosed. The control system controls the speed of a rotary motion motor that rotates the arm, the speed of the film transport motor and the distribution of those speeds, independently of each other. However, the apparatus is not adapted for use in an operating room on a patient in a prone position.

SUMMARY OF THE INVENTION

An x-ray apparatus is provided for cephalometric study of a patient in a prone position, where the cephalometric study can be repeated at a subsequent time, and a subsequent set of x-ray films essentially exactly overlay a previous set of x-ray films. The apparatus includes a frame, an extendable arm attached to the frame, and a receiver on the arm for holding an x-ray source. The receiver, and hence the x-ray source, can be placed in a variety of rigidly fixed and reproducible positions with respect to the frame, and with respect to a patient on a patient-supporting platform to which the frame is connected. A connector system provides a rigid connection between the frame and the patient-supporting platform, such as an operating table, bed, gurney or the like. The connector system fixes the relationship between the frame and the platform, and the frame can be disconnected from the platform, stored, and reconnected to the platform in an exact same position.

The platform is adapted with a headrest that receives the connector system for fastening the frame to the platform. The arm is connected to the frame through several pivot points or points of rotation, which allow the receiver for an x-ray source to be positioned in a variety of positions. Each pivot or rotation point has a locking mechanism for rigidly positioning the receiver and the x-ray source in a fixed and reproducible position. The arm is extendable and retractable, such as by telescopic or folding action, to place the x-ray source at different and reproducible focal lengths for producing images having a desired magnification and orientation.

In another aspect, an x-ray apparatus provides a panoramic x-ray machine for skeletal and dental studies. The apparatus has a frame that can be connected to a table or patient-supporting platform to provide a fixed relationship between the frame and the table and a patient on the table. The frame can then be non-moveably engaged with a floor, which provides a fixed relationship between the frame and the table, provided the table is non-moveably engaged with the floor. The frame can then be disconnected from the table, and the panoramic x-ray machine can be moved into position for taking a panoramic image of a patient's head, dentition, temporomandibular joint, and/or condyles. After a first panoramic image is taken, the frame can be disengaged from the floor, and the x-ray apparatus can be moved into storage or at least away from the table.

At a subsequent time, the x-ray apparatus can again be moved into position for engagement with the table. The frame can then again be connected to the table to provide a fixed relationship between the frame and the table, a relationship that is identical to the previously obtained relationship. Again, the frame can be locked into engagement with the floor, and the frame can be disconnected from the table. A second and subsequent panoramic image can be obtained. The patient can be either maintained in a fixed relationship with the table or repositioned in an exact same position with respect to the table. The frame can be repositioned in an exact same relationship with the table, so that the subsequent panoramic image overlays the initial panoramic image, which provides for ease of comparison.

In another aspect a panoramic x-ray machine and an extendable arm for holding a single-exposure x-ray source can both be mounted on a frame. A first set of images can be taken before surgery, and a surgical treatment objective can be traced onto the first set of images. An operation can be performed to move hard tissues, and while the patient is still on the operating table, a second set of images can be taken. The second set of images can be compared to the surgical treatment objective, and if necessary, additional surgery can be performed at that time while the patient is still under anesthesia. Thus, surgical results can be evaluated and surgery can be re-performed, if necessary, during a single period under anesthesia.

In another aspect, a method is provided for taking an x-ray of a patient in a horizontal position, where the x-ray is reproducible at a subsequent time. The method includes providing an x-ray source extendable to a fixed position with respect to a frame on which the x-ray source is movably mounted; connecting the frame to a patient-support platform on which a patient is resting in a prone position; taking a first x-ray of the patient or the patient's head; moving the x-ray source; and taking a second x-ray of the patient with the x-ray source in essentially the same position in which the x-ray source was located for taking the first x-ray.

BRIEF DESCRIPTION OF THE DRAWINGS

An embodiment of the invention is more fully described below with reference to the accompanying drawings, in which.

DETAILED DESCRIPTION OF INVENTION

Figure 1:
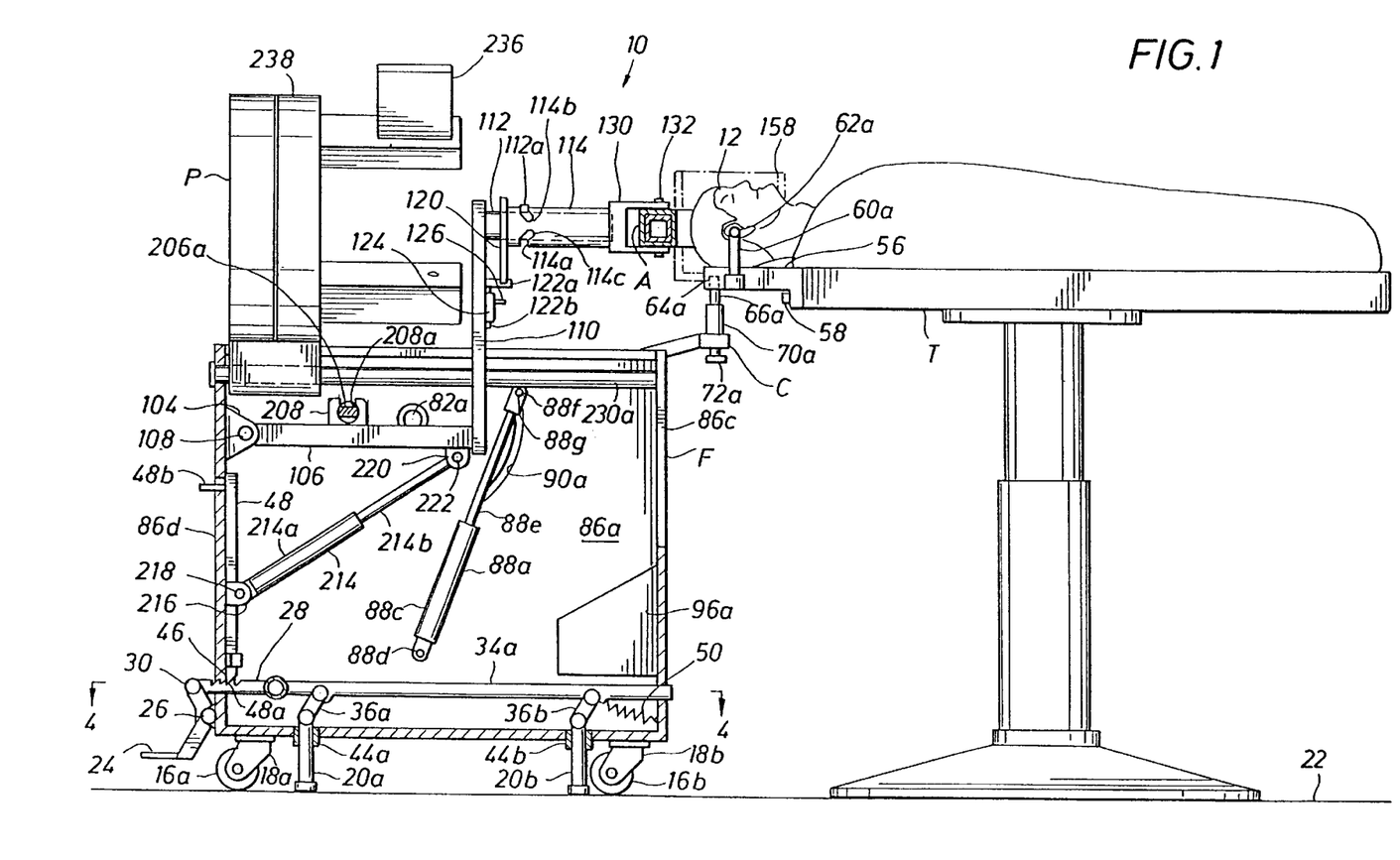
FIG. 1 is a side elevation in partial cross-section of an x-ray apparatus, according to the present invention.
Figure 2:
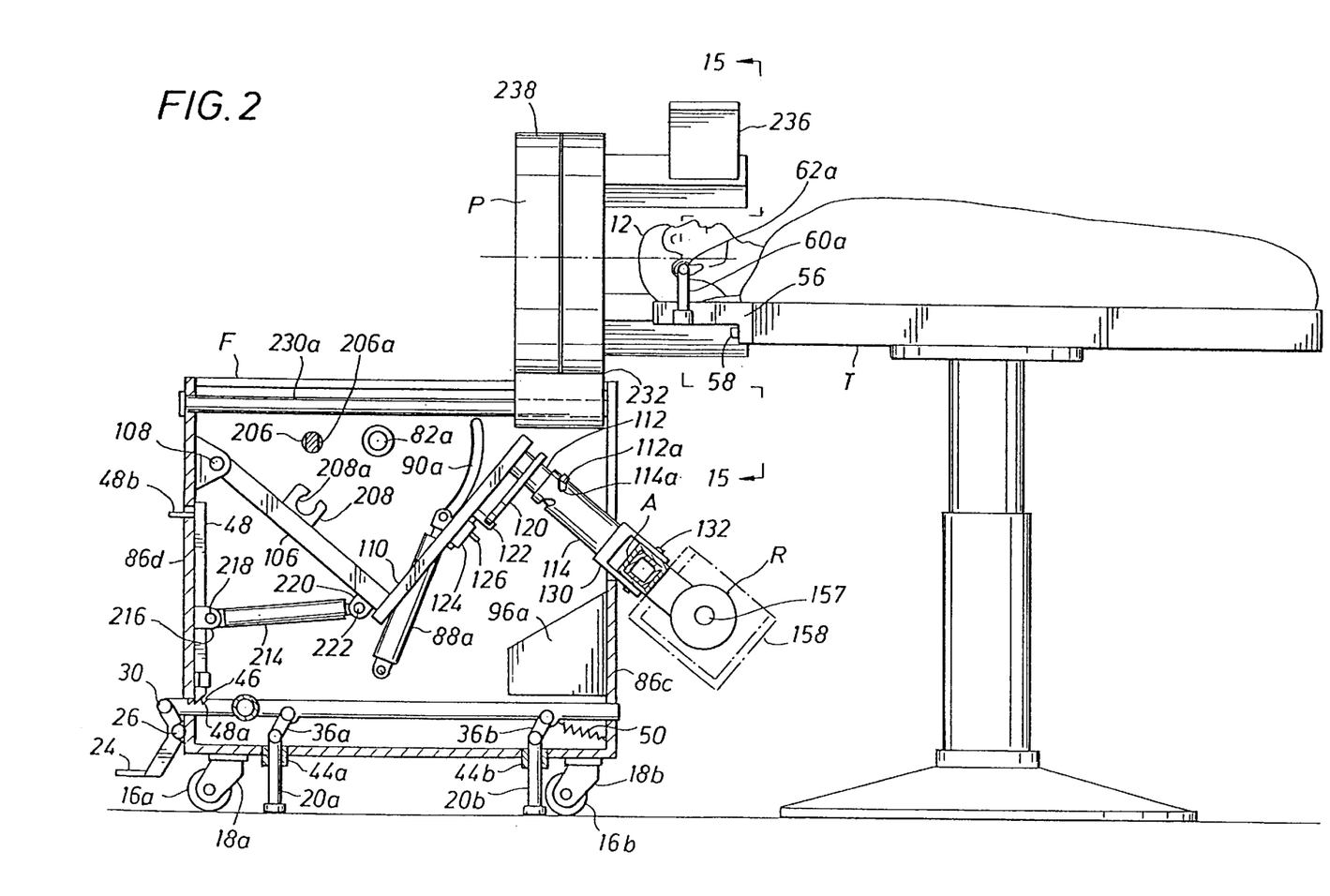
FIG. 2 is a side elevation in partial cross-section of the x-ray apparatus of FIG. 1 with a fixed-position arm moved into a stored position and a panoramic x-ray machine moved into an operative position.
Figures 3, 7:
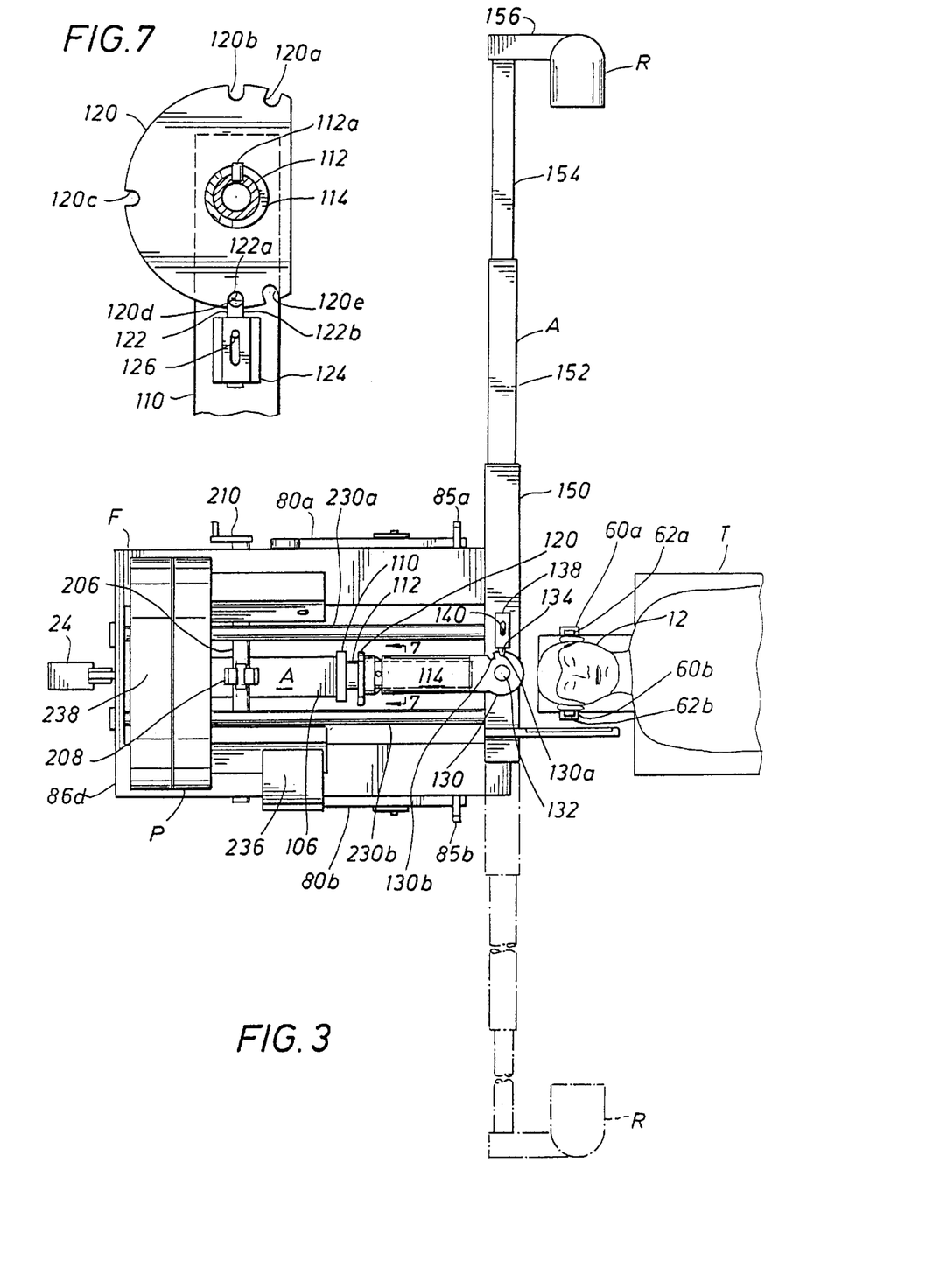
FIG. 3 is a top view of the x-ray apparatus of FIG. 1 showing an arm and an x-ray source receiver rotated and extended.
FIG. 7 is an elevation view of a locking mechanism as seen along the lines 7—7 in FIG. 3.

With reference to FIGS. 1–3, an x-ray apparatus 10 is shown for taking a standard set of x-ray's of a patient's head 12, while the patient is in a prone position on a table T, such as an operating table, bed, gurney or the like. Table T can be referred to generally as a platform for supporting a patient. A standard set of x-rays includes a right lateral cephalogram, an anterior-to-posterior cephalogram, and right and left transcranial views of the temporomandibular joint (TMJ). X-ray apparatus 10 includes a frame F and an extendable arm A mounted on frame F. A receiver R (FIG. 3) for holding an x-ray source is secured to arm A. A connector C connects frame F to table T and provides a fixed and reproducible relationship between frame F and table T. Arm A and receiver R can be fixed in several different locations for taking an x-ray of the patient's head 12. The positioning of receiver R and an x-ray source within receiver R is rigidly reproducible at a fixed focal length. Thus, a set of x-rays can be taken at one time and at a subsequent time with essentially identical magnification, orientation and location so that a second x-ray film can be compared to a first x-ray film.

For example, a set of x-ray films can be taken prior to an operation, and a surgical treatment objective can be overlaid on the first set of x-ray films. Frame F can be moved out of the way while surgery is performed and can be reconnected to the operating table T after the surgery is performed. A second set of x-ray films can then be taken for comparison of actual results to the surgical treatment objective. If desired results have not been obtained, additional surgery can be performed while the patient is still under anesthesia.

In the past, surgical results could not be adequately evaluated because a second set of x-rays did not have identical magnification, orientation and location as a first set of x-rays. Consequently, it was sometimes necessary to perform surgery a second time some days or weeks later after results were evaluated. The need for a second surgery some days or weeks after a first surgery is generally eliminated with use of x-ray apparatus 10.

In the illustrated embodiment, a panoramic x-ray machine P is mounted on frame F and can be moved into position for panoramic imaging of the patient's head 12. X-ray apparatus 10 can also be used for imaging other parts of a patient's body and for imaging animals and inanimate objects as well. The illustrated embodiment contemplates imaging by x-rays, but x-ray apparatus 10 can be adapted for use with other types of imaging systems requiring repeatable orientation and position. X-ray apparatus 10 is also illustrated as being portable, but alternatively, x-ray apparatus 10 can be fixed in position. The bed or table T can alternatively be moved into position for connection with frame F.

One of the primary advantages of x-ray apparatus 10 is its ability to fixedly and reproducibly locate an x-ray source at a desired focal length and position. Other advantages of x-ray apparatus 10 include its ability to provide reproducible panoramic images and its ability to provide a combination of panoramic images and fixed-position x-ray films. Also, instead of the x-ray source and associated film described herein, a digital x-ray system can be used.

Frame F is portable or movable and is exemplified as having four wheels 16a, 16b, 16c and 16d. Frame F can be portable by other means, such as by a guide rail system or by lifting or hoisting. Wheels 16a and 16c are mounted on swivel casters 18a and 18c, while wheels 16b and 16d are mounted on non-swivel casters 18b and 18d. Swivel casters 18a and 18c allow side-to-side pivoting of frame F for ease of attachment of connector C to table T. Frame F is illustrated as movable, but alternatively, Frame F can be fixed in position, such as to a floor or wall, and the patient can be moved to the x-ray apparatus while on a gurney, for example.

Figure 4:
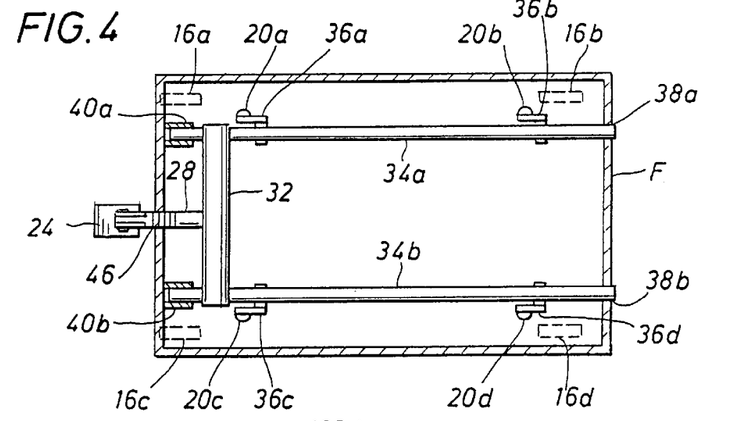
FIG. 4 is a sectional view of the x-ray apparatus of FIG. 1 as seen along the lines 4—4 in FIG. 1.

With reference to FIGS. 1 and 4, legs 20a, 20b, 20c and 20d are provided for fixing the position of frame F to a floor 22 after engaging connector C with table T, which is also fixed to floor 22. Legs 20 are engaged with floor 22 by stepping on a pedal 24. (Suffixes on like elements will be generally omitted for simplicity.) Pedal 24 is pivotally connected to frame F by a hinge 26 and to a rod 28 by a hinge 30. Rod 28 is connected to a bar 32, which is in turn connected to two parallel rods 34a and 34b. Bars 36a, 36b, 36c and 36d pivotally connect rods 34 to legs 20a, 20b, 20c and 20d, respectively. Frame F has openings 38a and 38b for receiving rods 34a and 34b, respectively. Frame F also has supports 40a and 40b for slideably receiving and supporting rods 34a and 34b, respectively.

Frame F can be rolled into position on wheels 16 and then fixed in a desired position by pressing on pedal 24 to engage legs 20 with floor 22. When an operator presses downward on pedal 24, rods 28 and 34 slide toward the operator, which causes bars 36 to push legs 20 downwardly through guides 44a, 44b, 44c and 44d, respectively, in frame F. Rod 28 has teeth 46, and frame F has a locking bar 48, which has an end 48a that engages teeth 46. The engagement of end 48a of locking bar 48 with teeth 46 on rod 28 locks rods 34 in a fixed position, which in turn locks legs 20 into engagement with floor 22. Locking bar 48 has a handle 48b, which can be lifted to disengage end 48a from teeth 46. A spring 50 pulls rod 34a, and hence legs 20, out of engagement and into a stored position, where legs 20 are raised above floor 22. Frame F is thus made portable in this example by use of wheels 16 and is fixed in a stationary position by legs 20. Frame F can be fixed in a stationary position by alternative means, such as by locking the wheels.

Figure 5:
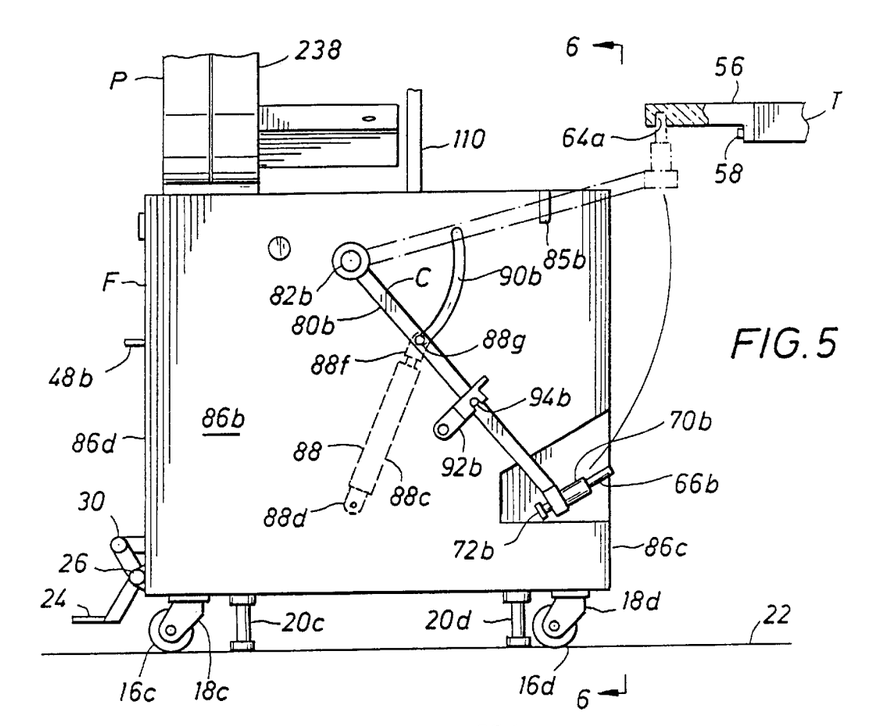
FIG. 5 is a partial side view of an x-ray apparatus, according to the present invention showing a connector arm moved into a stored position, where the fixed-position arm and receiver for the x-ray source have been cut-away for clarity.
Figure 6:
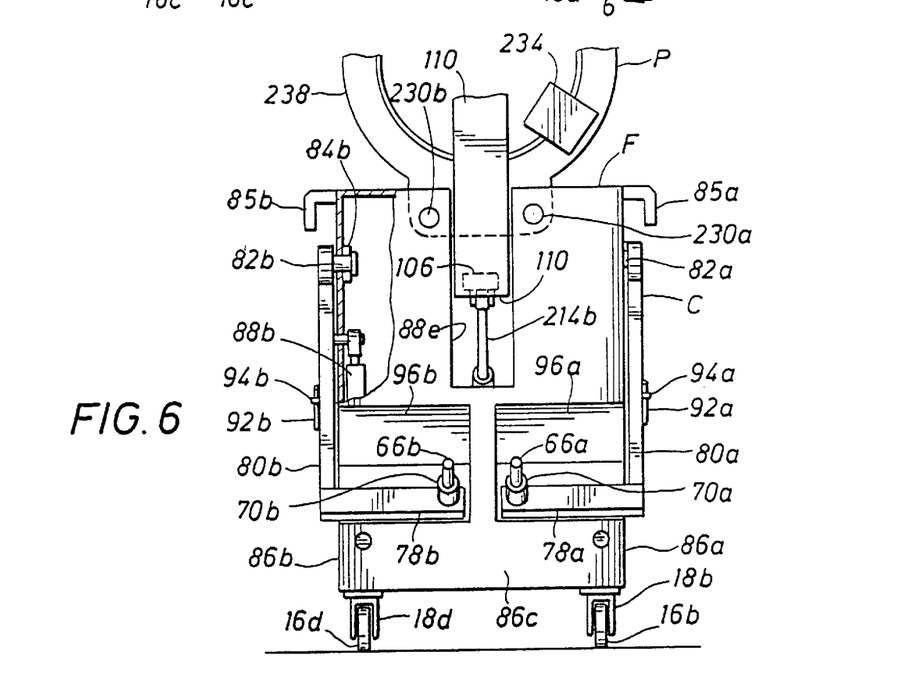
FIG. 6 is an end view of the x-ray apparatus of FIG. 5 as seen along the lines 6—6 in FIG. 5.
Figure 15:
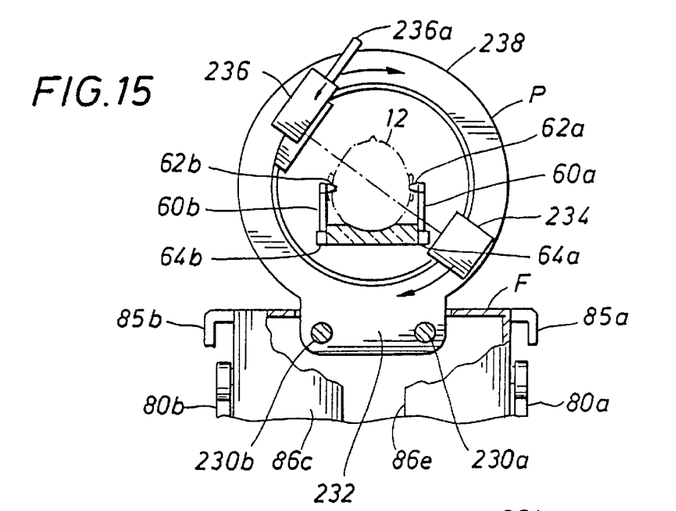
FIG. 15 is a partial sectional view of the x-ray apparatus of FIG. 2 as seen along the lines 15—15 in FIG. 2.

With reference primarily to FIGS. 1, 5 and 6, one embodiment of connector C is exemplified. Connector C attaches frame F to table T so that the position of frame F, and hence the position of arm A, is fixed with respect to table T and hence with respect to the patient. An adaptive headrest or cephalostat 56 is secured to table T by bolts 58. Headrest 56 is preferably made of a plastic material that allows passage of x-rays so that the headrest is not visible in an x-ray film. Headrest 56 has ear rods 60a and 60b (FIG. 15). Ear rods 60a and 60b have ear guides 62a and 62b, respectively, for engaging ear canals in the patient's head 12, and thus, headrest 56 includes a cephalostat. Ear guides 62a and 62b telescope inwardly symmetrically so that a patient's head can be located in a fixed and reproducible position. In this manner a set of x-rays can be taken at one time, and the patient's head can be repositioned on headrest 56 at a subsequent time in exactly the same position as the previous time. The position of the patient is thus fixed and reproducible.

As shown in FIGS. 1 and 5, headrest 56 has sockets 64a and 64b for receiving pins 66a and 66b, respectively, on connector C. Connector C has sleeves 70a and 70b for receiving pins 66a and 66b, respectively. Pin 66 is slideably engaged in sleeve 70 and is biased toward headrest 56 by a spring (not shown) within sleeve 70. Pins 66a and 66b have heads 72a and 72b, respectively. An operator can grasp head 72 to retract (and lock) pin 66 into sleeve 70 to engage or disengage pin 66 with socket 64 in headrest 56.

To connect frame F to table T, frame F is moved into a position so that pin 66a can be engaged with socket 64a by first pulling on head 72a to retract and lock pin 66a into sleeve 70a. Head 72a is then released so that pin 66a engages socket 64a. Swivel casters 18a and 18c allow frame F to be pivoted on wheel 16b so that pin 66b can be engaged with socket 64b. When both pins 66a and b are engaged with sockets 64a and 64b, respectively, in headrest 56, then the operator can press on pedal 24 to engage legs 20 with floor 22. This fixes the position of frame F with respect to table T, since both frame F and table T are now fixed to floor 22.

Turning now to FIG. 6, sleeves 70a and 70b are fastened to bars 78a and 78b, respectively, which are in turn connected to arms 80a and 80b, respectively. Arms 80a and 80b have shoulder pins 82a and 82b, respectively, which are engaged in support sockets 84a and 84b, respectively, in frame F. Stops 85a and 85b limit upward motion of arms 80a and 80b, respectively. A locking mechanism (not shown) can be provided on stops 85a and 85b to hold arms 80a and 80b, respectively, in an operative position.

Frame F has side walls 86a, 86b, 86c and 86d. Biasing elements 88a and 88b are connected to arms 80a and 80b, respectively, for holding pins 66 in engagement with sockets 64 in headrest 56. Although various types of biasing elements can be used, biasing elements 88a and 88b are exemplified as gas-filled shock absorbers. Each biasing element 88 has a body 88c, which has an end 88d pivotally connected to wall 86a or 86b of frame F (FIGS. 1 and 5). Each biasing element 88 also has a rod 88e slideably engaged with body 88c. Rod 88e is sealingly engaged with body 88c, which is filled with a gas so that rod 88e is biased outwardly. Rod 88e has an end 88f, and a pin 88g pivotally secures end 88f to arm 80. Wall 86a has an arcuate slot 90a, and wall 86b of frame F has an arcuate slot 90b through which pins 88g extend.

It is necessary for pins 88g to extend through the side walls of frame F since biasing element 88 is mounted on an inside surface of the walls of frame F while arms 80 are mounted outside of the walls of frame F. Arcuate slots 90a and 90b are provided along a radius from shoulder pins 82a and 82b, respectively. Latches 92a and 92b lock arms 80a and 80b, respectively, in a stored position. Arms 80a and 80b have pins 94a and 94b, respectively, for receiving latches 92a and 92b, respectively (FIGS. 5 and 6). Front wall 86c of frame F has recesses 96a and 96b for receiving bars 78a and 78b, respectively, of connector C. Recesses 96a and 96b allow pins 66a and 66b, respectively, to be stored without extending from front wall 86c of frame F.

Turning now to a discussion of arm A with reference to FIGS. 1 and 3, a support member 104 is attached, such as by welding, to an inside surface of back wall 86d of frame F. A bar 106 is pivotally connected to support 104 with a pin 108. A bar 110 is secured at a right angle to bar 106. A rod 112 is secured at a right angle to bar 110. A pipe 114 is engaged concentrically about rod 112. The engagement of pipe 114 about rod 112 provides a point of rotation for arm A. Pipe 114 has a slot 114a, which is generally circumferential about pipe 114. However, slot 114a has ends 114b and 114c that extend toward frame wall 86c for fixing arm A and receiver R in a desired location, as explained further below. Rod 112 has a pin 112a engaged in slot 114a for locating pipe 114 longitudinally with respect to rod 112, as explained further below.

With reference to FIG. 7, a locking plate 120 is provided for locking pipe 114 in a fixed position relative to rod 112. Locking plate 120 is secured to pipe 114 so that rotation of pipe 114 causes locking plate 120 to rotate. Locking plate 120 has notches 120a, 120b, 120c, 120d and 120e for receiving a locking pin 122. Locking pin 122 includes a first portion 122a that engages one of the notches on locking plate 120 and a second portion 122b at a right angle to first portion 122a. (FIG. 1) A biasing element 124 is mounted on bar 110, and second portion 122b of locking pin 122 is received through biasing element 124. A spring (not shown) is contained within biasing element 124 for pushing first portion 122a into engagement with, for example, notch 120d in locking plate 120. A handle 126 is provided on second portion 122b of locking pin 122 so that an operator can disengage locking pin 122 from one of the notches on locking plate 120.

An operator can pull on handle 126 to slide locking pin 122 out of engagement with locking plate 120 so that arm A can be rotated to a desired location. Notches 120a, 120b, 120c, 120d and 120e are provided at each of five desired locations for taking x-rays of the patient's head to provide x-ray films taken along a desired axis. The engagement of pin 112a with slot 114a and its ends 114b and 114c determines the lateral extension of pipe 114 along rod 112. The ends 114b and 114c are provided so that pipe 114 can slide along rod 112 away from the patient for clearance for particular x-ray shots, as explained further below.

A pivot head 130 is secured to pipe 114. Pivot head 130 and arm A have holes for receiving a pivot pin 132, which provides a pivot point for arm A about pivot head 130. Thus, arm A can pivot about pivot head 130 and rotate about rod 112 for locating receiver R in a desired location. With reference to FIG. 3, pivot head 130 has notches 130a and 130b, and a locking pin 134 is mounted on arm A for engagement with one of the notches on pivot head 130. Locking pin 134 is received in a biasing element 138, and a spring (not shown) is provided within biasing element 138 for pressing locking pin 134 into engagement with one of the notches on pivot head 130. A handle 140 is secured to locking pin 134 so that an operator can disengage locking pin 134 from a notch on pivot head 130.

Arm A is illustrated here as constructed of square or rectangular tubing having sections of successively smaller cross-section for providing a close-fitting telescoping action, but alternative configurations for arm A are also contemplated. For example, tubing with a circular cross section can be used in a telescoping action, and rather than a telescoping action, arm A can instead be folded at pivot points.

For the embodiment illustrated here and with reference to FIG. 3, arm A has a base section 150 that receives pivot pin 132. A middle section 152 telescopes within base section 150, and an end section 154 telescopes into middle section 152. A bar 156 is attached to end section 154, and receiver R is attached to bar 156. Receiver R receives and holds an x-ray source (not shown) in a fixed and locked position so that by locating receiver R in a fixed location, the x-ray source is thereby located in a fixed position. A suitable fixed-shot x-ray source can be obtained from Siemens Company, Dental Products Division, Charlotte, N.C., U.S.A., as well as from other manufacturers.

Receiver R can be repeatably located in a fixed position with respect to frame F, which can be located in a fixed position with respect to table T. A patient can be located in a fixed and repeatable position with respect to table T and headrest 56, so that the x-ray source can be located in a fixed and repeatable position with respect to the patient's head 12. A film holder 158 is secured to base section 150 for holding an x-ray film in a fixed and reproducible position. A recess 158a is provided on x-ray film holder 158 for receiving an x-ray film.

Figures 8, 9:
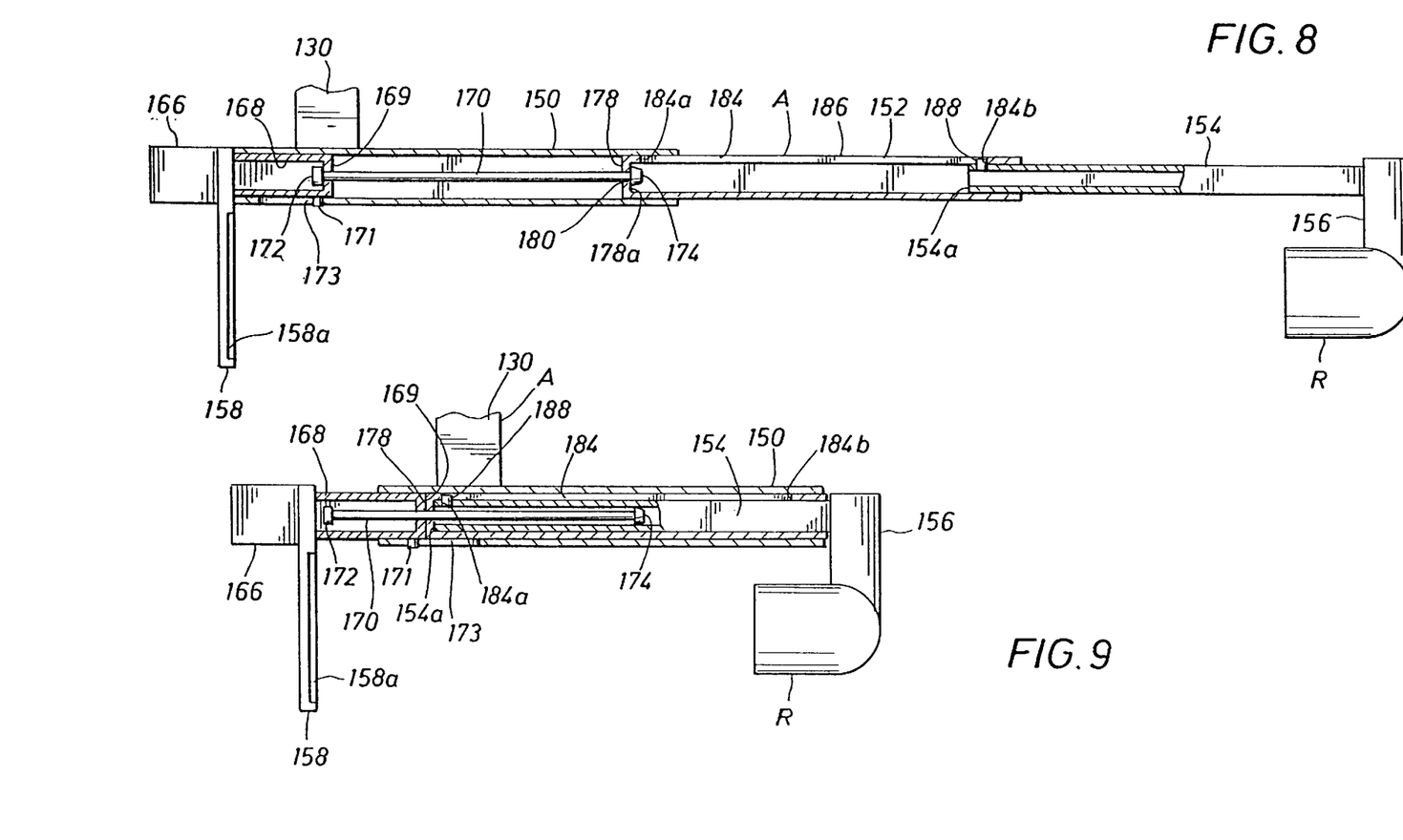
FIG. 8 is a partial cross-section of an extendable arm shown in its fully extended position, according to the present invention.
FIG. 9 is a partial cross-section of an extendable arm shown in its fully retracted position, according to the present invention.

Turning now to FIGS. 8 and 9, arm A is shown in partial cross section. Arm A extends outwardly so that receiver R is extended a fixed and reproducible distance from film holder 158. Arm A is shown here as requiring manual extension, but automated means can be used for extending receiver R from film holder 158, such as by use of hydraulic cylinders. Although other arrangements and other types of tubing can be used, square tubing is illustrated here, and middle section 152 slides within base section 150. Base section 150 has an inside dimension, and middle section 152 has an outside dimension that is nearly equal to the inside dimension of base section 150, within a relatively close tolerance, but allowing sliding movement. Similarly, end section 154 slides within middle section 152, again within a relatively close tolerance so that arm A is rigid when fully extended.

An image on an x-ray film held in film holder 158 is preferably reproducible from one time to the next within a tolerance of less than about 5 mm, preferably less than about 2 mm. The distance between a patient's mid-sagittal plane and film holder 158 is typically about 12.5 cm. The distance between the patient's mid-sagittal plane and an x-ray source for a lateral cephalogram is typically about 60 inches. Consequently, when arm A is fully extended, receiver R is preferably located in the same position from one time to the next within a radius from its longitudinal axis of less than about 50 mm, preferably less than about 20 mm.

Arm A has a film-holder end 166 and an interior tube 168 secured to end 166.

A rod 170 is received in base section 150, and rod 170 has heads 172 and 174.

Interior tube 168 has an opening 176 for receiving rod 170 in sliding engagement.

Middle section 152 has a closed end 178, which has an opening 180 for receiving rod 170 in sliding engagement with middle section 152. As shown in FIG. 8 middle section 152 can be extended outwardly from base section 150 until head 172 engages interior tube 168 and head 174 of rod 170 engages end 178 of middle section 152. In this manner, middle section 152 can be extended outwardly from base section 150 a fixed and reproducible distance. On the other hand, middle section 152 can be retracted into base section 150 until end 178 contacts interior tube 168, which again provides a fixed and reproducible position. (FIG. 9)

Middle section 152 has a slot 184 running longitudinally in a wall 186. Slot 184 has a first end 184a and a second end 184b. End section 154 has a pin 188 engaged with slot 184. Engagement of pin 188 with end 184b of slot 184 determines a maximum extension of end section 154 from middle section 152. Engagement of pin 188 with end 184a of slot 184 determines a fully-retracted position for end section 154 into middle section 152. In this manner end section 154 can be fully extended from middle section 152 or fully retracted into middle section 152 to provide two rigidly fixed and reproducible positions.

Receiver R has two fixed and reproducible positions with respect to film holder 158, a fully-retracted position and a fully-extended position. Arm A has a fully-retracted position, as shown in FIG. 9, which preferably places receiver R a distance of less than about 30 inches between an x-ray source received in receiver R and an x-ray film received in recess 158a in x-ray film holder 158. The distance can be adjusted to meet the requirements for standard x-rays. In this fully-retracted position, an end 169 of interior tube 168 is touching end 178 of middle section 152. End section 154 has an interior end 154a, and end 178 of middle section 152 has an inside surface 178a. In the fully-retracted position, end 154a touches interior surface 178a. In this manner, end section 154 has a fully-retracted position within middle section 152. Thus, there is a rigidly fixed and reproducible distance between receiver R and x-ray film holder 158, when arm A is in a fully-retracted position.

In a fully-extended position for arm A, middle section 152 is extended outwardly from base section 150 until head 172 engages an inside surface of end wall 169 of interior tube 168 and head 174 engages interior surface 178a of end 178 of middle section 152. End section 154 is extended fully from middle section 152 when pin 188 engages end 184b of slot 184. Bar 156 is rigidly connected to end section 154, and receiver R is rigidly connected to bar 156. An x-ray source 157 is rigidly received in receiver R (FIG. 2). In a fully-extended position for arm A, there is a rigidly fixed and reproducible distance between the x-ray source received in receiver R and an x-ray film received in recess 158a in x-ray film holder 158.

To lock arm A in a fully-extended or fully-retracted position, a spring-loaded pop-up button (not shown) can be placed on middle section 152 with a corresponding hole for the button in base section 150, for example. A button-and-hole combination can be used for each sliding joint for each desired position, as well as other locking mechanisms.

A cephalometric study can thus be conducted by positioning receiver R in various positions. Roentgenograms, photographs made with x-rays, and tomograms, which are three-dimensional images, can be produced, such as for studying a patient's maxillofacial and dental structures. A portable or movable x-ray apparatus is thus provided, such as for obtaining tomographs of a patient's dentition.

A lateral cephalogram can be taken by placing receiver R in a position perpendicular to a patient's mid-sagittal plane at a focal length of sixty inches between an x-ray source within receiver R and the patient's mid-sagittal plane. With reference to FIG. 3, receiver R is positioned on the patient's left side. Several joints must be locked to fix receiver R in a fixed location with respect to the patient. Arm A is rotated into position on the patient's left side by grasping handle 126 to disengage locking pin 122 from locking plate 120 (FIG. 7). Locking pin 122 is engaged with notch 120d on locking plate 120, which fixes the rotation of pipe 114 about rod 112. Floor 22 is a horizontal plane, and with locking pin 122 engaged with notch 120d on locking plate 120, arm A can be extended parallel to floor 22. If floor 22 is not a horizontal plane in reality, then legs 20 can be made adjustable, and a level indicator can be added to frame F or arm A.

For a lateral cephalogram taken perpendicular to the patient's mid-sagittal plane, handle 140 is moved to disengage locking pin 134 from pivot head 130 (FIG. 3). Handle 140 is released to engage locking pin 134 in notch 130a in pivot head 130, which fixes arm A so that arm A extends perpendicular to the patient's mid-sagittal plane. Thus, the engagement of locking pin 134 with a notch on pivot head 130 fixes the rotation of arm A about pin 132. Middle section 152 of arm A is extended fully from base section 150 until the heads of rod 70 are engaged as described above. End section 154 is fully extended from middle section 152 until pin 188 engages end 184b of slot 184 as described above (FIG. 8). In this manner an x-ray source received in receiver R is thus located in a rigidly fixed and reproducible position with respect to frame F, film holder 158, table T, and the patient's head 12.

A lateral cephalogram can be taken from the patient's right side by rotating arm A 180° about rod 112. This position is shown in phantom lines in FIG. 3. With reference to FIG. 7, handle 126 is grasped and pulled to disengage locking pin 122 from notch 120d on locking plate 120. Pipe 114 and arm A are rotated about rod 112 to align locking pin 122 with notch 120b on locking plate 120. Arm A is preferably retracted before the rotation is begun as this makes the rotation easier and less cumbersome. With locking pin 122 engaged with notch 120b, arm A extends parallel to floor 22. With locking pin 132 remaining engaged with notch 130a, arm A extends perpendicular to the patient's mid-sagittal plane on the patient's right side, as viewed in FIG. 3. Arm A can be fully extended to provide a fixed, rigid and reproducible location for receiver R on the patient's right side. An x-ray shot can then be taken to provide a roentgenogram. Frame F can be moved out of position by disconnecting connector C and can be subsequently re-positioned with re-connection of connector C. This places receiver R in the exact same location so that a subsequent roentgenogram can be taken that precisely overlays the previous roentgenogram.

Figures 10, 11:
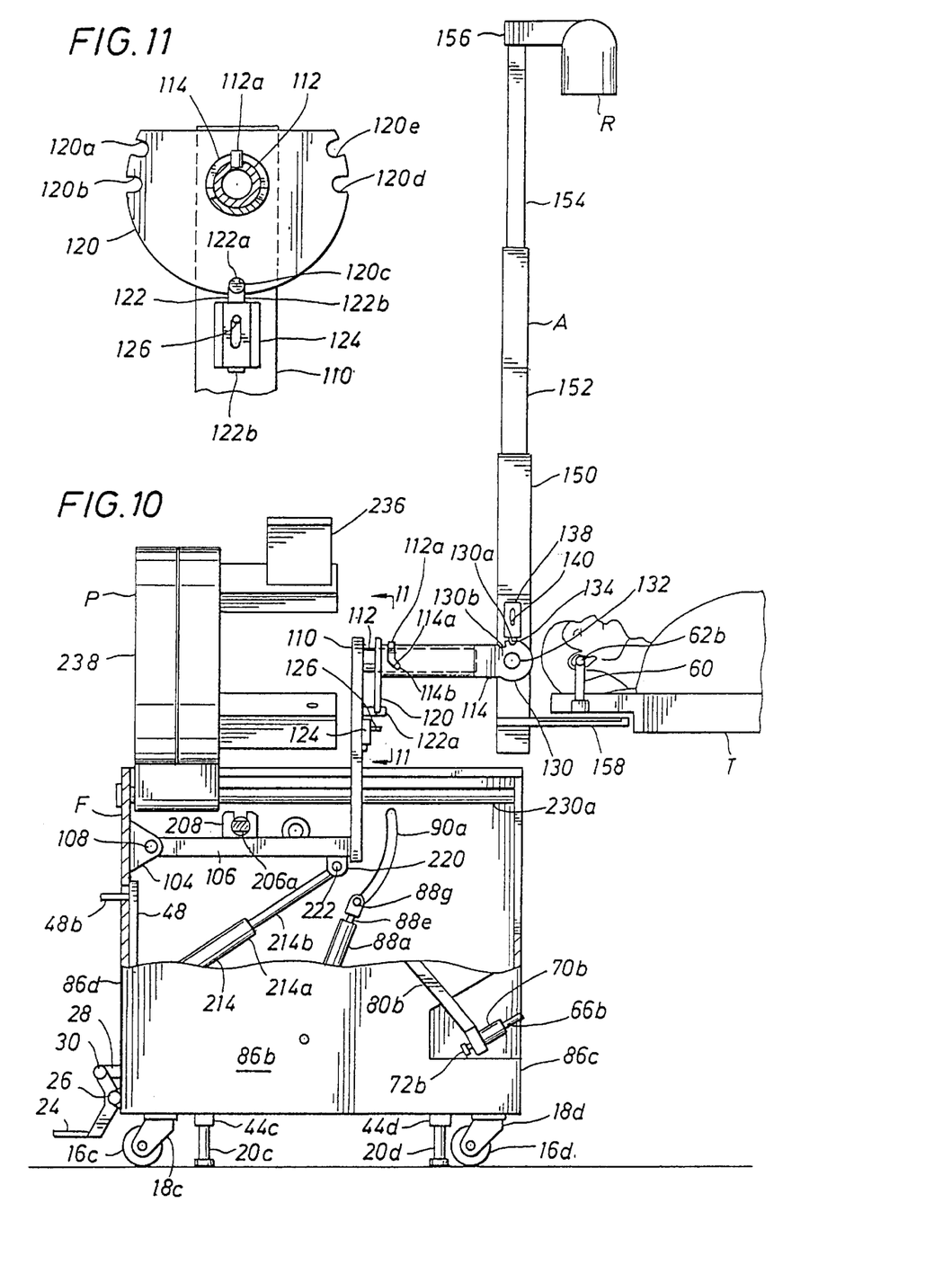
FIG. 10 is a partial side view of an x-ray apparatus according to the present invention showing an extendable arm and a receiver for an x-ray source and a vertical position.
FIG. 11 is a partial sectional view of a locking mechanism as seen along the lines 11—11 in FIG. 10.

Turning now to FIG. 10, an anterior-to-posterior cephalogram can be taken by rotating arm A above the patient to a vertical position. This rotation involves rotation of pipe 114 around rod 112. Locking pin 122 is disengaged from the notches on locking plate 120, and arm A is rotated into a vertical position with respect to floor 22. As shown in FIG. 11, locking pin 122 is engaged with notch 120c of locking plate 120 by release of handle 126 so that biasing element 124 pushes locking pin 122 into engagement with notch 120c. Locking pin 132 continues to be engaged with notch 130a in pivot head 130. Thus, no rotation of arm A about pin 32 on pivot head 130 is required for the left lateral cephalogram, the right lateral cephalogram or the anterior-to-posterior cephalogram. Notice that film holder 158 rotates into a desired position in all three of these positions for locating an x-ray film in a desired location with respect to an x-ray source received in receiver R and with respect to the patient's head 12.

Figure 12:
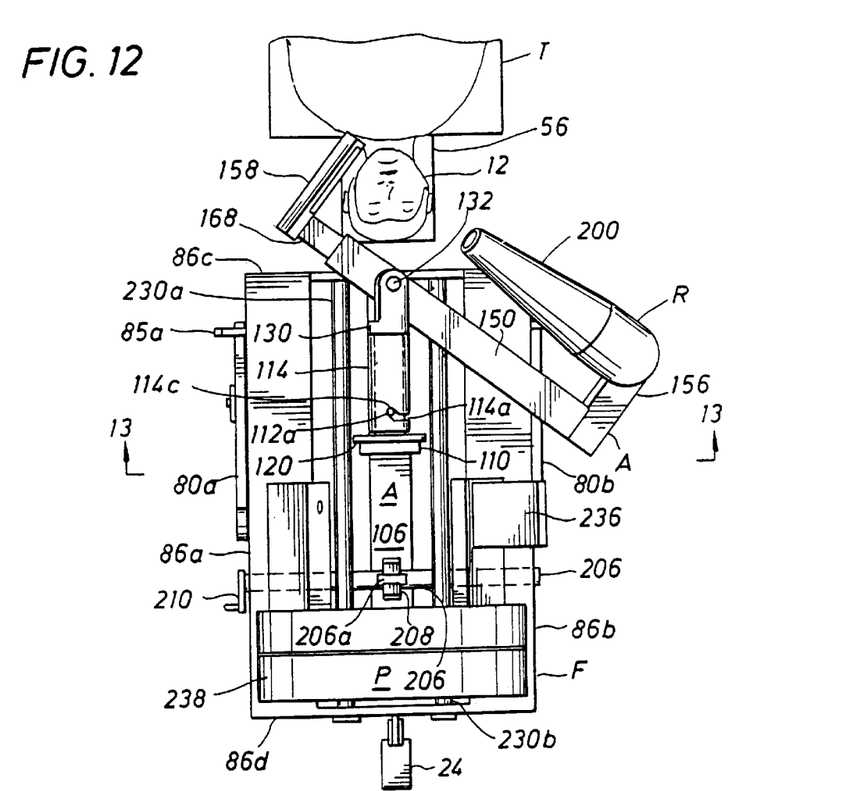
FIG. 12 is a top view of an x-ray apparatus showing a receiver for an x-ray source located at an angle with respect to the patient's mid-sagittal plane.
Figure 13:
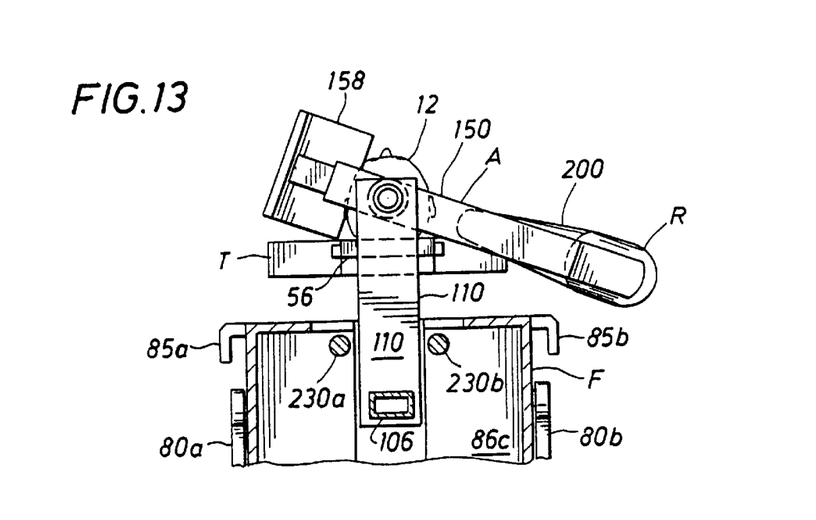
FIG. 13 is a sectional view of the x-ray apparatus of FIG. 12 as seen along the lines 13—13 in FIG. 12.

Turning now to FIGS. 12 and 13, for further cephalometric studies of a patient's dentition, temporomandibular joint (TMJ), and/or condyles, arm A can be retracted and rotated into a position where receiver R is located below the patient's head 12 and toward frame F. Surgeons and orthodontists prefer a roentgenogram taken along an axis to the mid-sagittal plane of about 20° from the Frankfurt plane and about 20° below a horizontal mid-plane passing through the patient's head when the patient is prone. These are standard right and left transcranial views of the temporomandibular joint, except for the fact that the patient is in a prone position. X-ray apparatus 10 accommodates these positions to provide a rigidly fixed and reproducible position for an x-ray source located in receiver R.

Figure 14:
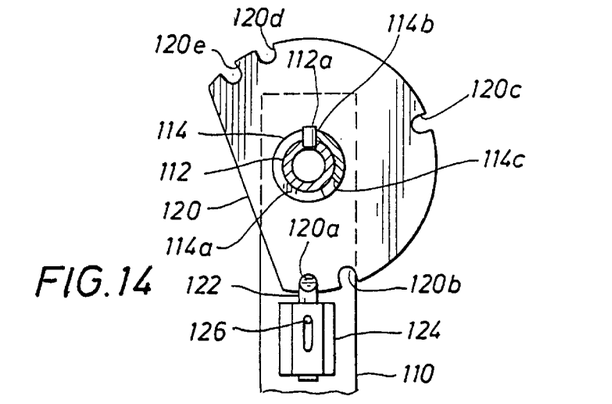
FIG. 14 is a partial sectional view of a locking mechanism of the x-ray apparatus in FIG. 12 as seen along the lines 14—14 in FIG. 12.

With reference to FIGS. 12–14, arm A is retracted and rotated into a position so that receiver R is toward frame F and below the patient's head 12. A focusing cone 200 is provided on receiver R for providing a narrow beam of x-rays through the patient's head 12 onto an x-ray film positioned in recess 158a in film holder 158. Arm A is placed in a retracted position as described above. Pipe 114 is rotated about rod 112 by disengaging locking pin 122 from the notches in locking plate 120. To lock receiver R in a position below the patient's head, pin 122 is engaged with either notch 120a or 120e. (FIG. 7) For the position illustrated in FIGS. 12 and 13, notch 120a is used. Notch 120a is located on locking plate 120 so that receiver R is placed at an angle of about 20° below the patient's head, when the patient is in a prone position. Locking plate 120 may have a series of notches so that receiver R can be moved through a range of angles from about 15° to about 30° in increments of about 5°.

To avoid a problem of clearance between film holder 158 and headrest 56, pipe 114 is slid longitudinally on rod 112 so that pin 112a engages end 114c of slot 114a, which moves arm A longitudinally along frame F. The curved nature of slot 114a allows for longitudinal movement of pipe 114 on rod 112, which in turn provides clearance for film holder 158 from headrest 56. Thus, when locking pin 122 is engaged with notches 120a or 120e, pin 112a is engaged with end 114c or 114a, respectively. Thus, notches 120a and 120e are provided to place arm A at an angle of about 70° with respect to floor 22.

To further provide clearance between film holder 158 and headrest or headrest 56, end 166 and interior tube 168 are slid away from pivot head 130. (FIG. 9) The extension of end 166 from pivot head 130 provides necessary clearance between film holder 158 and the patient's head 12 and headrest 56, when arm A is placed in the position illustrated in FIG. 12. A pin 171 is provided on interior tube 168, and a corresponding slot 173 in base section 150 receives pin 171 to prevent disengagement of end 166 from base section 150. A spring loaded, pop-up button can be placed on end 166 and a corresponding hole in base section 150 to further lock end 166 into a fixed and rigid engagement with base section 150.

To place receiver R toward frame F, rotation about pin 32 is required. With reference to FIG. 3, handle 140 is pulled to disengage locking pin 134 from a notch in pivot head 130. Arm A is rotated to move receiver R toward frame F, and then locking pin 134 is released. Biasing element 138 forces locking pin 134 into engagement with notch 130b.

By pushing arm A into a fully-retracted position, receiver R, and hence an x-ray source, are located in a rigidly fixed and reproducible position toward frame F and below the patient's head. Arm A can be maintained in a fully-retracted position provided sufficient friction between the sections prevents extension due to gravity. Alternatively, a locking mechanism, such as a pop-up button, can be provided to hold arm A in a fully-retracted position.

To rotate receiver R to the left side of the patient, locking pin 122 is disengaged from locking plate 120. Pipe 114 is rotated about rod 112, and pin 112a is moved within slot 114a until it engages end 114b. (FIGS. 12–14) Handle 126 is released to engage locking pin 122 with notch 120e, which rigidly and fixedly locates receiver R in position below the patient's head. This position would be about 20° below a horizontal plane passing through the center of the patient's head. A range of angles may be provided as discussed above with reference to the right transcranial TMJ view. In re-positioning receiver R from the right side of the patient to the left side of the patient, it is not necessary to disengage locking pin 134 from notch 130b in pivot head 130 (FIG. 3).

Thus, a full set of fixed-position x-rays can be taken for a cephalometric study of a patient's dental-facial structure. By rotating arm A as described above, receiver R and an x-ray source received therein can be positioned to take standard left and right lateral cephalograms, a standard anterior-to-posterior cephalogram, and standard left and right transcranial views of the temporomandibular joints. The cephalograms can be taken again at a subsequent time, and receiver R and an x-ray source therein can be positioned again in the earlier locations to provide a duplicate set of roentgenograms.

In this manner, an oral surgeon and an orthodontist or dental-facial orthopedist can take a pre-surgery x-ray, overlay a surgical treatment objective, and move the portable x-ray apparatus 10 out of the way while surgery is performed. After surgery, and while the patent is still under anesthesia, portable x-ray apparatus 10 can be reconnected using connector C to again fix x-ray apparatus 10 in position with respect to table T. A second set of x-rays can then be taken, which are essentially exactly from the same position as taken earlier, so that the second set of x-rays can be compared to the surgical treatment objective to determine whether the surgical results are satisfactory. If the surgical results are not satisfactory, then additional work can be done while the patient remains under anesthesia. In the past, the second set of x-rays would have been taken days later and could not be compared to earlier sets of x-rays. In the past, if the surgical results were unsatisfactory, the patient would have to be operated upon a second time, resulting in additional discomfort, inconvenience and expense. Such second surgeries are generally rendered unnecessary when x-ray apparatus 10 is used.

With reference to FIGS. 1 and 3, arm A and bar 106 are held in an operative position by a bar 206. Bar 106 has a pair of projections 208, and each projection 208 has a curved inner surface 208a. Bar 206 generally has a circular cross-section, but bar 206 has a rectangular cross-section 206a for engagement with curved inner surfaces 208a of projections 208 (FIG. 1). Bar 206 has a handle 210 for engaging rectangular cross-section 206a with projections 208 (FIG. 3). Handle 210 normally hangs downwardly under the force of gravity when projections 208 are not engaged with rectangular cross-section 206a. This orients cross-section 206a for insertion into projections 208. After cross-section 206a is inserted into projections 208 by lifting arm A and bar 106 upwardly into engagement with bar 206, handle 210 is rotated 90° to rotate bar 206 for engagement of rectangular cross-section 206a with curved interior surfaces 208a. Arm A can thus be locked into a rigidly fixed and reproducible position with respect to pivoting about pin 108.

With reference to FIG. 1, a biasing element 214 is fixed between wall 86d of frame F and bar 106 of arm A. A support 216 is attached, such as by welding, to wall 86d, and a pin 218 provides a pivotal connection between biasing element 214 and support 216. A support 220 is attached to bar 106, and a pin 222 provides a pivotal connection for biasing element 214. Biasing element 214 has a body 214a and a shaft 214b. Shaft 214b slides into and out of body 214a. Body 214a can be a gas-filled shock absorber, or it can contain a spring for assisting in lifting arm A into position. Other types of biasing elements, including, for example, a counterweight system, can be used for biasing elements 214 and 88.

With reference to FIG. 2, arm A is moved into a stored position by disengaging rectangular cross-section 206a from projections 208 using handle 210 (FIG. 3). Arm A is fully retracted, and pivot head 130 is pushed downwardly, sliding shaft 214b into body 214a of biasing element 214. If biasing element 214 is very strong, a locking mechanism (not shown) can be provided to hold arm A down in a stored position, as illustrated in FIG. 2. With reference to FIG. 6, frame F has a slot 86e. Pivot head 130 and pipe 114 of arm A are received in slot 86e of frame F in the stored position for arm A shown in FIG. 2. With arm A thus stored, connector C can be disconnected from table T, and by pulling up on handle 48b, legs 20 can be disengaged from floor 22 so that portable x-ray apparatus 10 can be rolled away from table T.

With reference to FIGS. 2 and 15, panoramic x-ray machine P is slid into an operative position when arm A is in its stored position within slot 86e. Rods 230a and 230b are fastened within frame F between walls 86c and 86d. X-ray machine P is slidable along rods 230a and 230b and tolerances are relatively tight so that x-ray machine P can be positioned in a rigidly fixed and reproducible position from one time to the next.

To use panoramic x-ray machine P, arm A is pushed downwardly into its stored position and connector C is disconnected from table T. It is necessary to disconnect connector C and pin 66 from socket 64 so that x-ray machine P can sweep around the patient's head 12 without interference. Since table T is fixed to floor 22, and frame F is fixed to floor 22 by legs 20, the relationship between frame F and table T remains fixed after connector C is disconnected.

Referring to FIG. 2, panoramic x-ray machine P is pushed toward the patient until there is contact between a wall 232 on x-ray machine P and an inside surface of wall 86c on frame F. Panoramic x-ray machine P can be adapted from a commercially-available panoramic x-ray machine, such as an Orthophos® Plus panoramic x-ray machine from Siemens Company, Dental Products Division, in Charlotte, N.C., U.S.A.

With reference to FIG. 15, panoramic x-ray machine P has an x-ray source 234 and an x-ray film holder 236. Panoramic x-ray machine P has a cylindrical section 238, and a motor (not shown) and a gear system (not shown) are enclosed in cylindrical section 238. The motor and gear system drive x-ray source 234 and x-ray film holder 236 in a circumferential arc about the patient's head 12. A panographic x-ray image is taken of the patient's dental facial structure. Film holder 236 has a motor means (not shown) for moving a film cartridge 236a through film holder 236 as x-ray source 234 and film holder 236 revolve around cylindrical section 238. Thus, a sweeping panographic image is taken of the patient's head for cephalometric study. Headrest 56, ear post 60 and ear guides 62 are preferably constructed of a material to provide minimal interference with and minimal shadows on the panographic roetgenogram.

After a panoramic x-ray film has been taken, panoramic x-ray machine P is slid along rods 230a and 230b (FIG. 3) to a stored position away from the patient, as shown in FIG. 1. By lifting upward on handle 48b, end 48a of locking bar 48 is disengaged from teeth 46 on rod 28. Spring 50 pulls rods 34a, 34b and 28, so that legs 20 are thus disengaged from floor 22. Portable x-ray apparatus 10 can then be moved away from table T.

In summary, portable x-ray apparatus 10 can be connected to a patient-supporting platform, such as operating table T, using connector C to provide a rigidly fixed and reproducible relationship between frame F and table T. Table T can be adapted with headrest 56, and a patient can be located in a fixed and reproducible position using ear guides 62a and 62b in engagement with the patient's ear canals. Thus, the relationship between frame F and the patient's head 12 is rigidly fixed and reproducible from one time to a subsequent time.

Arm A can be extended and locked into at least five different fixed and reproducible positions, as described above, for taking standard cephalograms while the patient is in a prone position A cephalmetric study can thus be conducted by taking lateral cephalograms from each or either side of the patient, an anterior-to-posterior cephalogram by placing receiver R above the patient, and right and left transcranial TMJ views by placing receiver R in the positions described with reference to FIGS. 12 and 13. A first set of cephalograms can be taken before surgery or before any other procedure, such as orthodontics and a second set can be taken after the procedure. X-ray apparatus 10 can be moved away from table T during the procedure and relocated in the exact same position with respect to table T after the procedure is completed.

The focal length is exactly reproducible from one time to the next by extension or retraction of arm A, which provides reproducible magnification of an image from one time to the next. The rigidity of frame F and arm A is such that receiver R can repeatedly hold an x-ray source in an essentially exact and reproducible position from one time to the next, so that a subsequent x-ray film can be overlaid onto a previous x-ray film for comparison purposes. In this manner the results achieved by surgery or similar procedures can be compared to a treatment objective, such as a surgical treatment objective. A surgical treatment objective can be overlaid on a first x-ray film, and a second x-ray film taken after completion of the treatment can be compared to the surgical treatment objective. If necessary, the treatment can be modified or repeated, such as while the patient is still under anesthesia, to obtain the surgical treatment objective.

Similarly, panoramic x-ray images can be taken before and after a treatment for comparison of the second set to the first set of x-rays. It is necessary to disconnect frame F from table T while taking panoramic x-ray films, but the relationship between frame F and table T and the patient's head 12 remains fixed, since frame F and table T are each fixed to floor 22. Thus, an x-ray source can be positioned in a rigidly fixed and reproducible position with arm A and in a revolving and reproducible position with panoramic x-ray machine P.

An apparatus has thus been disclosed as one embodiment of the present invention. A method is also disclosed for taking an x-ray of a patient, where the x-ray is reproducible at a subsequent time. The patient may be in a horizontal position, although the method and apparatus has application for taking x-rays of a patient in a non-horizontal position. Further, the x-rays may be taken of the patient's head, although the method and apparatus has application for taking x-rays of other body parts of the patient or of an animal.

The method includes providing an x-ray source extendable to a fixed position with respect to a frame on which the x-ray source is movably mounted; connecting the frame to a patient-support platform (on which a patient can be resting in a prone position); taking a first x-ray of the patient, preferably of the patient's head; moving the x-ray source; and taking a second x-ray of the patient with the x-ray source in essentially the same position in which the x-ray source was located for taking the first x-ray. The second x-ray is essentially identical in magnification, orientation and location as the first x-ray so that comparison can be made.

Thus, a surgical treatment objective can be traced onto the first x-ray, surgery can be performed, and the second x-ray can be used to evaluate surgical results. A full set of standard x-rays can be taken, and non-standard x-rays can also be taken. The method can also include disconnecting the frame from the patient-support platform after taking the first x-ray and before taking the second x-ray; reconnecting the frame to the patient-support platform before taking the second x-ray; disconnecting the frame from the patient-support platform; and taking a panoramic x-ray of the patient's head.

Additional aspects of the method can optionally include fixing the position of the frame with respect to a floor after connecting the frame to the patient-support platform; providing the x-ray source movably mounted to a frame in an operating room; adapting an operating table with a headrest capable of connection to the frame; moving the frame into a position for connection to the operating table; connecting the frame to the headrest on the operating table; taking a first set of x-rays of the patient's head; moving the frame away from the patient-support platform; performing surgery on the patient's head; reconnecting the frame to the patient-support platform; and taking a second set of x-rays with the x-ray source in essentially the same locations as used for taking the first set of x-rays.

The foregoing disclosure and description of the invention are illustrative and explanatory thereof, and various changes in the details of the illustrated apparatus and construction and method of operation may be made without departing from the spirit of the invention.

I claim:

1. A method for taking an x-ray of a patient lying on a patient-support platform, the x-ray being reproducible at a subsequent time, comprising:

providing an x-ray source extendable to a fixed position with respect to a frame on which the x-ray source is movably mounted;

connecting the frame to the patient-support platform;

fixing the patient's head in a fixed position with respect to the x-ray source;

extending the x-ray source away from the patient's midsagittal plane;

taking a first lateral cephalogram from a point that is to the side of the patient at a first focal length; and moving the x-ray source to take a cephalogram having a second focal length that is different from the first focal length.

2. The method of claim 1, further comprising taking a second lateral cephalogram of the patient with the x-ray source in essentially the same position in which the x-ray source was located for taking the first lateral cephalogram and disconnecting the frame from the patient-support platform before taking the second lateral cephalogram.

3. The method of claim 2, further comprising reconnecting the frame to the patient-support platform before taking the second lateral cephalogram, wherein the step of moving the x-ray source to take a cephalogram having a second focal length includes retracting the x-ray source; providing a point of rotation for rotating the x-ray source in a horizontal plane; and moving the x-ray source to a point where the x-ray source is below the patient's head for taking a transcranial cephalogram.

4. The method of claim 1, further comprising:

providing a panorama x-ray machine on the frame; and taking a panoramic x-ray of the patient's head.

5. The method of claim 1, wherein the step of fixing the patient's head in a fixed position includes providing a cephalostat on the patient-support platform; providing an arm for holding the x-ray source; and fixing a film holder to the cephalostat and to the arm for rigidly fixing the x-ray source with respect to the patient's head.

6. The method of claim 1, further comprising:

providing the x-ray source movably mounted to the frame in an operating room;

adapting an operating table with a headrest capable of connection to the frame, wherein the operating table serves as the patient-support platform;

connecting the frame to the headrest on the operating table;

taking a first set of x-rays of the patient's head;

moving the frame away from the patient-support platform;

performing surgery on the patient's head;

reconnecting the frame to the patient-support platform; and taking a second set of x-rays with the x-ray source in essentially the same locations as used for taking the first set of x-rays.

7. The method of claim 6, further comprising determining a surgical treatment objective before surgery; placing the patient under anesthesia; and evaluating the results of the surgery by comparing the second set of x-rays to the surgical treatment objective while the patient remains under anesthesia.

8. The method of claim 1, further comprising:

taking a first set of x-rays;

determining a surgical treatment objective;

placing the patient under anesthesia;

performing surgery on the patient;

taking a second set of x-rays; and evaluating surgical results by comparing the second set of x-rays to the surgical treatment objective while the patient remains under anesthesia so that additional surgery can be performed, if necessary, during a single period under anesthesia.

9. An x-ray apparatus for taking x-rays of a patient lying on a patient-support platform, comprising:

a frame;

a connector capable of connecting the frame to the patient-support platform;

a movable arm connected to the frame; and a receiver for receiving an x-ray source, the receiver being secured to the arm and repeatably movable to fixed locations with respect to the frame;

wherein the arm is adapted to extend the receiver away from the mid-sagittal plane of the patient's head for taking a cephalogram from the patient's side;

wherein the arm is adapted to take cephalograms at two or more different focal lengths; and wherein the apparatus is adapted to provide a fixed relationship between the patient's head and the x-ray source.

10. The x-ray apparatus of claim 9, wherein the frame and movable arm are adapted to provide a point of rotation for the arm in a vertical plane and a point of rotation for the arm in a horizontal plane.

11. The x-ray apparatus of claim 9, further comprising an x-ray film holder secured to the arm at an end opposite the receiver.

12. The x-ray apparatus of claim 10, wherein the frame and movable arm include:

a cart;

an arm-mounting assembly secured to the cart, the arm-mounting assembly providing the point of rotation for the arm in a vertical plane; and a pivot head secured to the arm-mounting assembly, wherein the arm is pivotally connected to the pivot head for providing the point of rotation for the arm in a horizontal plane.

13. The x-ray apparatus of claim 9, further comprising an x-ray source received in the receiver.

14. An x-ray apparatus, comprising:

a frame;

a connector capable of connecting the frame to a patient-support platform;

a movable arm connected to the frame;

a receiver for receiving an x-ray source, the receiver being secured to the arm, wherein the receiver is repeatably movable to a fixed location with respect to the frame; and a panorama x-ray machine secured to the frame for taking a panoramic x-ray film.

15. The x-ray apparatus of claim 14, wherein the x-ray machine is movably engaged with the frame for positioning the panorama x-ray machine between an operative position and a stored position.

16. The x-ray apparatus of claim 14, where in the panorama x-ray machine is oriented for taking a panoramic x-ray of a patient in a prone position.

17. The x-ray apparatus of claim 16, wherein the frame has two rods, and the panorama x-ray machine is slidable on the two rods.

18. The x-ray apparatus of claim 14, wherein the panorama x-ray machine has an x-ray source movable in an arcuate path in a vertical plane.

19. The x-ray apparatus of claim 12, wherein the cart has wheels for providing portability and a locking mechanism for securing the frame in a fixed position.

20. The x-ray apparatus of claim 19, wherein the connector includes a pair of connecting arms pivotally connected to the frame.

21. The x-ray apparatus of claim 20, further comprising a headrest adapted for connection to the patient-support platform, the headrest having a receptor for receiving the connector.

22. The x-ray apparatus of claim 21, wherein the headrest has ear guides for engaging a patient's ear canals for fixedly locating a patient's head on the headrest.

23. The x-ray apparatus of claim 22, wherein the connector includes a pair of connecting arms, each connecting arm having a pin, the receptor on the headrest including a pair of sockets, one socket for receiving one pin on one connecting arm for rigidly fixing the relation between the frame and the patient-support platform.

24. The x-ray apparatus of claim 9, wherein the arm includes a bracket pivotally connected to the frame, a rotatable shaft engaged with the bracket and an extendable member pivotally connected to the rotatable shaft.

25. The x-ray apparatus of claim 24, wherein the extendable member extends by telescopic action, the receiver being connected to the extendable member.

26. The x-ray apparatus of claim 9, wherein the frame is movable.

27. The x-ray apparatus of claim 26, wherein wheels are attached to the frame for making the x-ray apparatus portable, further comprising a mechanism for making the frame non-movable.

28. An x-ray apparatus for taking a panoramic x-ray of a patient in a prone position on a patient-support platform having a cephalostat for holding the patient's head in a fixed position, comprising:

a frame;

a connector for securing the frame in a fixed relationship with respect to the patient;

a panorama x-ray machine movably engaged with the frame, the panorama x-ray machine having a cylindrical section for surrounding the patient's head;

an x-ray source received in the cylindrical section of the panorama x-ray machine, the x-ray source being movable in an arcuate path in a vertical plane within the cylindrical section; and a film holder maintained opposite the x-ray source as the x-ray source moves, wherein an x-ray film is advanced in the film holder as the x-ray source revolves in the cylindrical section for taking a sweeping panographic x-ray image of the patient's dental-facial structure.

29. The x-ray apparatus of claim 28, further comprising a headrest adapted for connection to the patient-support platform, the headrest receiving the connector and the cephalostat.

30. The x-ray apparatus of claim 28, wherein the frame comprises a portable cart having wheels and a pair of rods spaced apart in a parallel configuration, the panorama x-ray machine being received on and slideable on the pair of rods.

31. The x-ray apparatus of claim 29, wherein the connector includes a pair of connecting arms pivotally engaged with the frame, the frame comprises a wheeled cart for rolling on a floor and a pair of horizontal rods spaced apart in a parallel configuration, and wherein the panorama x-ray machine slides back and forth on the pair of rods.

32. The x-ray apparatus of claim 28, further comprising an arm rigidly extendable from the frame, the arm having an outer end, the outer end having a receiver for holding an x-ray source in a fixed position with respect to the frame.

33. An x-ray apparatus, comprising:

a frame;

an arm extendable from the frame, the arm being adapted for receiving an x-ray source and holding the x-ray source in a fixed and reproducible location with respect to the frame; and a panorama x-ray machine secured to the frame.

34. The x-ray apparatus of claim 33, wherein the panorama x-ray machine has an x-ray source movable in a vertical plane.

35. The x-ray apparatus of claim 33, wherein the extendable arm has a fixed position for taking a lateral cephalogram transverse to a patient's sagittal plane.

36. The x-ray apparatus of claim 35, wherein the extendable arm has a fixed position providing a 60-inch focal length.

37. The x-ray apparatus of claim 33, wherein the frame is movable so that the x-ray apparatus is portable.

38. The x-ray apparatus of claim 33, further comprising a connector attached to the frame for connecting the frame to a table.

39. An apparatus for taking cephalograms of a patient lying on a patient-support platform, comprising:
  a cephalostat for holding the patient's head in a fixed position; and
  an arm adapted for holding an x-ray source in a fixed position with respect to the patient's head, wherein the arm is adapted for taking x-rays at two or more different focal lengths from the side of the patient.

40. The x-apparatus of claim 39, wherein the apparatus is further adapted for taking a transcranial cephalogram.

41. The x-ray apparatus of claim 39, wherein the arm is further adapted for taking a transcranial cephalogram.

42. An x-ray apparatus for taking standard cephalograms of a patient lying on a patient-support platform, comprising:
  a frame;
  a plurality of wheels mounted below the frame so that the frame can be moved;
  a plurality of legs adapted for extending below the frame for fixing the position of the frame;
  an arm-support member pivotally connected to the frame, the arm-support member having a rotatable member;
  a pivot head connected to the rotatable member;
  an arm including:
    a fixed member pivotally secured to the pivot head;
    an extendable member that is capable of extension and retraction with respect to the frame; and
    a receiver connected to the extendable member;
  an x-ray source located in the receiver;
  a biasing element connected between the frame and the arm-support member for assisting in movement of the arm-support member; and
  a plurality locking mechanisms for fixing the x-ray source in an operative position.

43. The x-ray apparatus of claim 42, wherein the patient-support platform includes a cephalostat for holding the patient's head, further comprising a pair of arms pivotally attached to the frame for connecting the frame to the patient-support platform for rigidly fixing the relationship between the patient's head and the x-ray source.

44. The x-ray apparatus of claim 42, wherein the patient-support platform includes a cephalostat for holding the patient's head, further comprising a film holder connected to and between the arm and the cephalostat for rigidly fixing the relationship between the patient's head and the x-ray source.

* * * * *